United States Patent [19]

Kagawa et al.

[11] Patent Number: 5,218,036
[45] Date of Patent: Jun. 8, 1993

[54] SHRINKABLE FILM FROM ETHYLENE-VINYL ACETATE POLYMER TALC AND ETHYLENE-PROPYLENE COPOLYMERS BLEND

[75] Inventors: Seiji Kagawa; Hideaki Toda; Yoshinaga Murakami, all of Kanagawa, Japan

[73] Assignee: Tonen Sekiyukagaku K.K., Tokyo, Japan

[21] Appl. No.: 630,810

[22] Filed: Dec. 24, 1990

Related U.S. Application Data

[63] Continuation of Ser. No. 144,362, Jan. 15, 1988, abandoned.

[30] Foreign Application Priority Data

Jan. 19, 1987 [JP] Japan ................. 62-5639[U]
Jan. 19, 1987 [JP] Japan ................. 62-5640[U]
Jan. 19, 1987 [JP] Japan ................. 62-9519[U]

[51] Int. Cl.$^5$ ............ C08K 3/34; C08L 31/04; C08L 47/00
[52] U.S. Cl. .................... 524/451; 524/524
[58] Field of Search ............... 524/451, 524

[56] References Cited

U.S. PATENT DOCUMENTS

| | | | |
|---|---|---|---|
| 3,821,333 | 6/1974 | Goodwin | 525/222 |
| 4,243,576 | 1/1981 | Fischer | 525/222 |
| 4,303,571 | 12/1981 | Jansen et al. | |
| 4,336,212 | 6/1982 | Yoshimura et al. | |
| 4,425,268 | 1/1984 | Cooper | 525/222 |
| 4,436,863 | 3/1984 | Albee | 524/451 |
| 4,497,936 | 2/1985 | Tancrede | 525/222 |
| 4,621,114 | 11/1986 | Watanabe | 524/451 |
| 4,743,636 | 5/1988 | Bersano | 524/451 |

FOREIGN PATENT DOCUMENTS 0201331 11/1986 European Pat. Off.
1533280 7/1968 France.
18567 6/1973 Japan.

Primary Examiner—Christopher Henderson
Attorney, Agent, or Firm—Armstrong, Westerman, Hattori, McLeland & Naughton

[57] ABSTRACT

Shrinkable film and articles prepared therefrom which shrink more than 5% when heated to a temperature of 50° C. are disclosed. The shrinkable film is prepared by stretching a polymer film of EPDM or EPM and EVA and talc more than 1.5 times in at least one direction at specified temperatures.

2 Claims, 1 Drawing Sheet

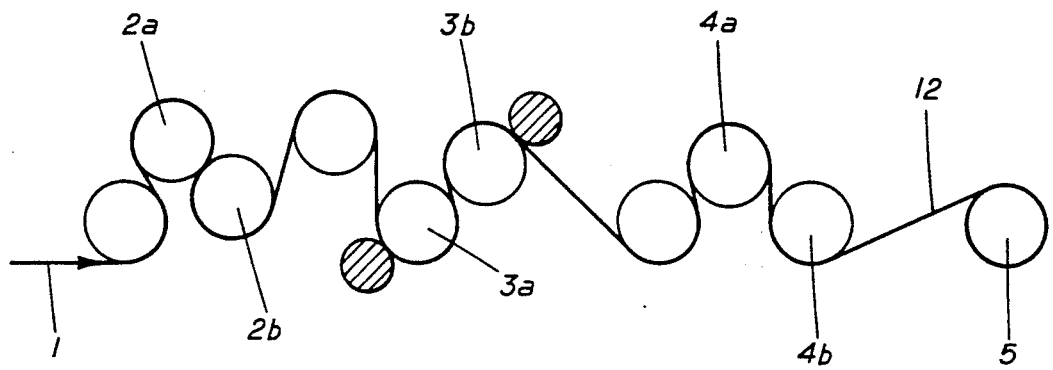
FIG. 1
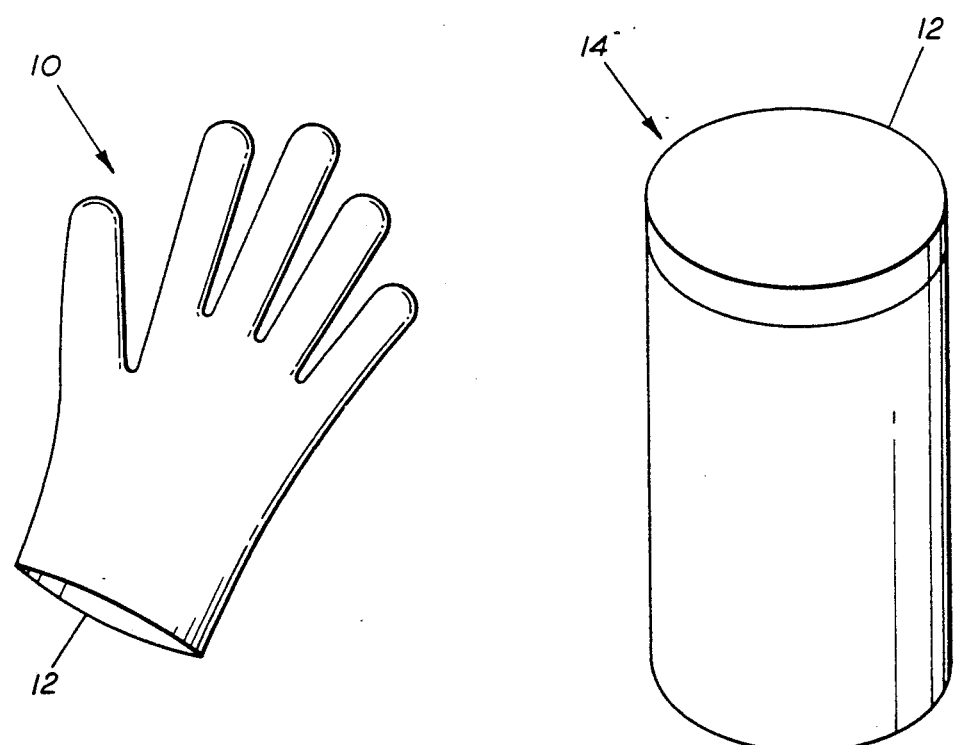
FIG. 2
FIG. 3

SHRINKABLE FILM FROM ETHYLENE-VINYL ACETATE POLYMER TALC AND ETHYLENE-PROPYLENE COPOLYMERS BLEND

This application is a continuation of application Ser. No. 07/144,362 filed Jan. 15, 1988, abandoned.

BACKGROUND OF THE INVENTION

1. Field of the Invention

The present invention relates to shrinkable films and to shrinkable articles prepared therefrom, and more particularly, it relates to films which shrink up to about 50% or more at a low temperature.

More particularly, the present invention relates to a process for producing and articles produced from low-temperature shrinkable film which exhibits a heat shrinkage close to 50% at temperatures ranging from the heat-set temperature to the stretching temperature, said process comprising stretching a polymer film composed of EPDM or EPM, EVA, and talc in a specific ratio more than 1.5 times in at least one direction at a temperature lower than 50° C. and heat-setting the stretched film at a temperature lower than the stretching temperature.

2. Description of the Prior Art

The conventional known process for producing the above-mentioned heat shrinkable film involves the stretching (in one direction or two directions) and winding without heat setting. The conventional heat shrinkable film, therefore, shrinks at a temperature range at which stretching has been accomplished. However, there has been no heat shrinkable film which exhibits a great heat shrinkage at a temperature below 50° C.

For example, polyethylene film stretched at 100°–150° C. begins to shrink at about 120° C. Polypropylene film stretched at about 120° C. begins to shrink at about 130° C. Polyvinyl chloride film stretched at 100°–120° C. begins to shrink at 120° C. Polyvinylidene chloride film stretched at 20°–50° C. begins to shrink at 50°–100° C. The last one is one example which shrinks at low temperatures; but the shrinkage at 50°–60° C. is rather small.

In other words, there has not yet been developed heat-shrinkable film which shrinks more than 50% at a temperature below 50° C.

Heat shrinkable film which exhibits a great shrinkage at low temperatures is expected to find diverse uses as exemplified in the following.

(1) Shrink packaging and sealing of medical and research materials which need low temperature storage or freeze storage (e.g., cap seal of frozen stock tube).

(2) Contact packaging for those products which are not suitable for heating after packaging. Film for contact packaging should conform itself to the size or shape of the object upon heating at a low temperature (e.g., packaging of fresh produce).

(3) Disposable gloves which tightly fit hands upon slight heating of gloved hands. Tight-fitting gloves improve work efficiency.

(4) Protection of gypsum and bandage from wetting and staining, utilizing the ability of shrink film to tightly fit them with ease.

In the field of medical service, gloves are commonly used at the time of blood collecting, operation, and examination. These gloves are required to be disposable for the prevention of infection.

In the field of electronics industry, too, disposable gloves are used for the prevention of environmental pollution.

Disposable gloves are finding more uses in barber shops and beauty parlors and households where cleanliness is required.

For the above-mentioned uses, there are several kinds of disposable gloves, but most of them are on the large side so that they suit many different people. Such gloves are loose and uncomfortable and give the wearer a feeling of physical disorder which decreases work efficiency.

For this reason, there has been a demand for inexpensive, disposable gloves which tightly fit the hands of individuals, without giving the fingers a feeling of physical disorder.

It is a common practice to protect an injured hand or leg with bandage or gypsum, and it is desirable that the bandage or gypsum should be provided with a protective cover when the injured person takes a bath.

It is desirable that those who work in a dusty environment should put protective covers on their hands and legs to keep off dusts. Some machine parts also need protective covers for the same purpose. For safety and hygiene, protective covers which tightly fit the objects are necessary.

Protective covers made of plastics are available in the form of bags in different sizes; but most of them are on the large side so that they suit many different people. Such protective covers are loose and uncomfortable; and they are imperfect to protect bandage or gypsum from wetting and prone to decrease work efficiency.

For this reason, there has been a demand for inexpensive disposable protective covers which tightly fit the objects (such as bandage and gypsum), without giving the wearer a feeling of looseness and physical disorder.

The present invention was completed to solve the above-mentioned problems involved in the prior art technology. Accordingly, it is an object of the present device to provide a heat shrinkable film capable of shrinking as much as 50% at a temperature below about 50° C. Another object of the present invention is to provide inexpensive, disposable gloves which tightly fit the hands of different sizes of individuals, without giving the fingers a feeling of physical disorder and decreasing work efficiency. Another object of the present invention is to provide an inexpensive, disposable, shrinkable protective cover which fits an object and protects it from wetting and dust.

SUMMARY OF THE INVENTION

The shrinkable film of the present invention shrinks at least 5% or more when heated to a temperature of 50° C.

Since the shrinkable articles pertaining to the present invention are formed from film which shrinks at least 5% or more when heated to a temperature of 50° C., they tightly fit the hands when they are heated to 30°–50° C. after they have been put on the hands, even though they are slightly oversized. Therefore, they do not give the fingers a feeling of physical disorder and decrease work efficiency. Moreover, they are inexpensive and disposable.

BRIEF DESCRIPTION OF THE DRAWINGS:

FIG. 1 illustrates the process for producing the low-temperature shrinkable film which is used in the present device.

FIG. 2 illustrates a shrinkable glove pertaining to the present device.

FIG. 3 illustrates a shrinkable protective cover pertaining to the present device.

DETAILED DESCRIPTION OF THE INVENTION

Shrinkable film and articles produced therefrom will now be described in detail.

According to the present invention, the low-temperature shrinkable film is produced by stretching a polymer film, composed of EPDM or EPM, EVA, and talc, as shown below in (A), more than 1.5 times in at least one direction under the temperature conditions shown below in (B).

(A) The formulation of EPDM or EPM, EVA, and talc
  EPDM or EPM: 40-70 wt. %
  EVA (containing more than 10 wt. % of VA): 30-60 wt. % Talc: 5-15 wt. %

(B) Temperature conditions
  Preliminary heating temperature: 40°-45° C.
  Heat-stretching temperature: 45°-55° C.
  Cooling temperature (heat-setting and annealing): lower than the heat-stretching temperature (specifically 20°-40° C.

The term EPDM or EPM as used herein refers to ethylene-propylene-diene elastomer terpolymer or ethylene-propylene elastomer copolymer, respectively.

The EPDM contains as a third component a non-conjugated diene such as hexadiene, dicyclopentadiene, ethylidenenorbornene, methylenenorbornene, propylidenenorbornene, and methyltetrahydroindene.

Any known EPDM or EPM can be used in the present device.

The amount of EPDM or EPM in the shrinkable film should be 40-70 wt. % as mentioned above. With an amount less than 40 wt. %, the resulting film is undesirably sticky. Conversely, with an amount in excess of 70 wt. %, the film formability is undesirably poor.

The term EVA as used herein refers to ethylene-vinyl acetate copolymer. The one containing more than 10 wt. % of vinyl acetate (VA) is desirable. With a VA content lower than 10 wt. %, the resulting film is undesirably poor in low-temperature stretchability.

The amount of EVA in the shrinkable film should be 30-60 wt. % as mentioned above. With an amount less than 30 wt. %, the film formability is undesirably poor. Conversely, with an amount in excess of 60 wt. %, the resulting film has an undesirably low elasticity.

The talc used in the present device is a typical substance as a filler (usually in the leafy or flaky form) having the composition of $3MgO \cdot 4SiO_2 \cdot H_2O$.

The amount of talc in the shrinkable film should be 5-15 wt. % as mentioned above. With an amount less than 5 wt. %, the resulting film is prone to blocking. Conversely, with an amount in excess of 15%, the resulting film is poor in stretchability. The talc may be replaced by calcium carbonate or barium sulfate.

According to the present invention, the above-mentioned EPDM or EPM, EVA and talc are mixed in a predetermined ratio, the resulting compound is formed into a polymer film (unstretched film), and the film is stretched under the temperature condition (B) specified above. In this way there is obtained the low-temperature shrinkable film of the present invention.

To be more specific, as shown in FIG. 1, unstretched film 1 is passed through a pair of pre-heating rolls 2a and 2b, a pair of heat-stretching rolls 3a and 3b, and finally a pair of cooling (heat-setting) rolls 4a and 4b, and the thus stretched film 12 is wound up onto the take-up roll 5.

The film stretching ratio can be controlled by changing the rotational speeds of heat-stretching rolls 3a and 3b. In other words, the heat-stretching roll 3a is run slow and the heat-stretching roll 3b is run fast.

The production of the low-temperature shrinkable film 12 of the present invention is explained with reference to the following example and the physical properties of the shrinkable film are shown in the following.

A 150-mm thick unstretched polymer film composed of 55 wt. % of EPDM, 35 wt. % of EVA (containing more than 28 wt. % of VA), and 10 wt. % of talc was stretched 2.0 to 5.0 times under the following temperature conditions to give low-temperature shrinkable film:
Preliminary heating temperature: 40° C.
Heat-stretching temperature: 50° C.
Cooling temperature (heat-setting): 20° C.

The shrinkage of the resulting low-temperature shrinkable film was measured in the following manner. The results are shown in Table 1.

(1.) Dimension of test piece
120 mm (in stretch direction) × 15 mm (for MD stretching)
120 mm (in stretch direction) × 15 mm (for TD stretching)
(MD denotes the longitudinal direction parallel to the film running direction, and TD denotes the crosswise direction perpendicular to MD.)

(2.) A water bath was used to effect shrinkage, and the dipping time was 3 seconds.

(3.) The shrinkage was calculated according to the following formula.

$$MD \text{ shrinkage } (\%) = \frac{120 - A}{120} \cdot 100$$

where A is the length of the test piece measured in MD direction after shrinkage.

$$TD \text{ shrinkage } (\%) = \frac{120 - B}{120} \cdot 100$$

where B is the length of the test piece measured in TD direction after shrinkage.

TABLE 1

| Temp. of water bath | Di- rec- tion | Shrinkage Times and direction of stretching | | | | | |
|---|---|---|---|---|---|---|---|
| | | Not stretched | 2.0 MD | 3.0 MD | 4.0 MD | 5.0 MD | 2.5 MD |
| 30° C. | MD | 0.8 | 0.8 | 2.7 | 3.5 | 2.0 | 0 |
| | TD | 0 | −0.3 | −0.5 | −1.0 | −0.8 | 2.1 |
| 40° C. | MD | 1.5 | 8.3 | 10.0 | 10.5 | 11.5 | 0.9 |
| | TD | −0.7 | −2.5 | −2.7 | −3.3 | −5.0 | 6.7 |
| 50° C. | MD | 9.0 | 32.5 | 43.4 | 46.5 | 46.5 | 6.8 |
| | TD | −4.0 | −12.0 | −12.3 | −12.8 | −13.5 | 27.7 |

As shown by the results of the measurement of shrinkage, the low-temperature shrinkable film of the present invention exhibits a shrinkage as high as about 50% at 50° C. in the case where the stretching is 5.0.

According to the present invention, a shrinkable glove 10 is formed from low-temperature shrinkable film 12 which, upon heating to a temperature of 50° C. with hot water or hot air, shrinks more than 50% and at least more than 5%, preferably more than 10%, and more desirably more than 15%.

It is desirable that the shrinkable protective glove 10 made of the low-temperature shrinkable film 12 should be heated to a temperature of about 30°-50° C. at the time of use.

As shown in FIG. 2, the shrinkable glove 10 of the present invention is produced from two sheets of the above-mentioned low-temperature shrinkable film 12 by heat sealing in hand shape. (When heat sealing is performed, the entire film except the sealing part is insulated from heat.) The shrinkable glove can also be produced from the low-temperature shrinkable film 12 by sewing instead of heat sealing.

The above-obtained low-temperature shrinkable film was made into a shrinkable glove measuring 28 cm long and 25 cm wide. The glove was dipped in hot water at 40° C. for 5 seconds, whereupon it shrank to 25 cm in length and 22 cm in width. The shrinkage in the lengthwise direction was 12.0% and the shrinkage in the widthwise direction was 10.7%.

When the hand wearing the shrinkable glove was dipped in hot water at 40° C. for 5 seconds, it uniformly shrank to tightly fit the hand and fingers.

After use, the shrinkable glove can be easily removed by tearing the plastic film.

The above-mentioned low-temperature shrinkable glove 10 tightly fits the hand, giving a soft feeling. It prevents the grasped object from slipping off and helps to work smoothly. Moreover, it is inexpensive and can be made into disposable gloves. It is suitable for coloring and secondary fabrication such as embossing.

Since the shrinkable gloves pertaining to the present invention are formed from plastic film which shrinks more than 5% when heated to a temperature of 50° C., they tightly fit the hands when they are heated to 30°-50° C. after they have been put on the hands, even though they are slightly oversized. Therefore, they do not give the fingers a feeling of physical disorder and do not decrease work efficiency. Moreover, they are inexpensive and disposable.

According to the present invention, a shrinkable protective cover 14 is formed from film 12 which, upon heating to a temperature of 50° C. with hot water or hot air, shrinks more than 5%, preferably more than 10%, and more desirably more than 15%.

It is desirable that the shrinkable protective cover 14 made of the low-temperature shrinkable film should be heated to a temperature of about 30° to 50° C. at the time of use.

The shrinkable protective cover 14 of the present invention is produced from the above-described low-temperature shrinkable film 12, with the ends thereof joined together by heat sealing. (When heat sealing is performed, the entire film except the sealing part is insulated from heat.) The shrinkable protective cover 14 can also be produced from the low-temperature shrinkable film 12 by sewing instead of heat sealing.

A low-temperature shrinkable film prepared in the manner described above was made into a shrinkable protective cover in bag form measuring 60 cm long and 25 cm wide. The protective cover was dipped in hot water at 45° C. for 3 seconds, whereupon it shrank to 48 cm in length and 19 cm in width. The shrinkage in the lengthwise direction was 20% and the shrinkage in the widthwise direction was 24%.

The shrinkable protective cover was put on bandage and then dipped in hot water at 45° C. for 3 seconds. It uniformly shrank to tightly cover the bandage.

After use, the protective cover can be easily removed by tearing the plastics film in the MD direction.

Since the shrinkable protective cover pertaining to the present device is formed from film which shrinks more than 5% when heated to a temperature of 50° C., it tightly fits the object (such as bandage and gypsum) when it is heated to 30°-50° C. after it has been put on the object even though it is slightly oversized. Therefore, it protects the object from wetting, without giving the wearer a feeling of looseness and physical disorder and decreasing work efficiency. Moreover, it is inexpensive and disposable.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

What is claimed is:

1. A low-temperature shrinkable film capable of shrinking by 5-50% at a temperature up to 50° C., comprising a film made of a polymer composition consisting essentially of from about 30 to about 60 wt. % ethylene-vinyl acetate polymer having more than about 10 wt. % vinyl acetate, from about 5 to 15 wt. % talc and from about 40 to about 70 wt. % of an elastomer selected from ethylene-propylene-diene terpolymer and ethylene-propylene copolymer, said shrinkable film being prepared by passing an unstretched film of the polymer composition through pre-heating rolls, heat-stretching rolls and cooling rolls continuously, so that said unstretched film is heated to a temperature of from about 40° C. to about 50° C., heat stretched more than 1.5 times in at least one direction at a temperature of from about 45° C. to about 55° C. and then cooled.

2. Shrinkable article comprising a film of claim 1.

* * * * *